(12) United States Patent
Simmons et al.

(10) Patent No.: US 8,647,315 B2
(45) Date of Patent: Feb. 11, 2014

(54) MEDICAL CANISTER CONNECTORS

(75) Inventors: Tyler Simmons, San Antonio, TX (US); Alexander Sammons, San Antonio, TX (US); Kenneth Knowles, Bandera, TX (US)

(73) Assignee: KCI Licensing, Inc., San Antonio, TX (US)

( * ) Notice: Subject to any disclaimer, the term of this patent is extended or adjusted under 35 U.S.C. 154(b) by 12 days.

(21) Appl. No.: 13/450,140

(22) Filed: Apr. 18, 2012

(65) Prior Publication Data

US 2012/0204405 A1    Aug. 16, 2012

Related U.S. Application Data

(62) Division of application No. 12/467,153, filed on May 15, 2009, now Pat. No. 8,216,197.

(60) Provisional application No. 61/109,439, filed on Oct. 29, 2008.

(51) Int. Cl.
*A61M 1/00* (2006.01)

(52) U.S. Cl.
USPC ............ 604/319; 604/27; 604/35; 604/65; 604/118; 604/119; 604/317; 604/318; 604/322; 604/326; 137/205; 141/35; 141/59; 141/65; 141/95; 141/198; 119/14.46

(58) Field of Classification Search
USPC .......... 604/317, 318, 319, 322, 326; 156/242, 156/243

See application file for complete search history.

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |

(Continued)

FOREIGN PATENT DOCUMENTS

| AU | 550575 A1 | 8/1982 |
| AU | 745271 | 4/1999 |

(Continued)

OTHER PUBLICATIONS

International Search Report for corresponding PCT Application No. PCT/US2009/044244 mailed Oct. 6, 2009.

(Continued)

*Primary Examiner* — Tatyana Zalukaeva
*Assistant Examiner* — Ilya Treyger

(57) ABSTRACT

A medical canister connector is presented for connecting to a medical canister, which has a patient port and a reduced-pressure port. The medical canister connector includes a first connection member that is coupled to a patient-port-attachment member, which is for coupling to a patient port on a medical canister and has a patient-port opening with a first longitudinal axis. The medical canister connector also includes a second connection member coupled to a reduced-pressure-port-attachment member, which is for coupling to a reduced-pressure port on the medical canister and has a reduced-pressure-port opening with a second longitudinal axis. A spacing member or pressure transport member may be used to couple the first connection member to the second connection member. The spacing member or transport member flexes and twists during connection. The medical canister connector may also help organize one or more pressure-sensing conduits. Methods are also presented.

6 Claims, 4 Drawing Sheets

(56) References Cited

U.S. PATENT DOCUMENTS

| | | |
|---|---|---|
| 2,969,057 A | 1/1961 | Simmons |
| 3,066,672 A | 12/1962 | Crosby Jr. et al. |
| 3,367,332 A | 2/1968 | Groves |
| 3,520,300 A | 7/1970 | Flower, Jr. |
| 3,556,101 A | 1/1971 | Economou |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,830,238 A | 8/1974 | Kurtz et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,637,103 A | 6/1997 | Kerwin et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2058227 A | 4/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | WO96/34636 A | 11/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

(56) References Cited

OTHER PUBLICATIONS

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

MEDICAL CANISTER CONNECTORS

RELATED APPLICATION

The present invention is a divisional of U.S. patent application Ser. No. 12/467,153, entitled "Medical Canister Connectors," filed on May 15, 2009 now U.S. Pat. No. 8,216,197 which claims the benefit, under 35 USC §119(e), of the filing of U.S. Provisional Patent Application Ser. No. 61/109,439, entitled "A Medical Canister Connector," filed Oct. 29, 2008. All of these applications are incorporated herein by reference for all purposes.

BACKGROUND

The present invention relates generally to medical treatment systems and, more particularly, to medical canister connectors and methods.

In a number of medical applications, fluids, such as blood, ascites, and exudates from wounds, are removed from a patient and need to be stored for disposal or processing. The removal of these fluids may be the primary purpose of a treatment or a secondary result. For example, in many surgical procedures, it is common to apply suction to remove blood. As another example, in applying reduced-pressure therapy, or negative pressure wound therapy, fluids are removed and must be stored or processed.

The removed fluids are often stored in medical canisters. The medical canisters receive fluids from the patient and receive suction, or reduced pressure, from a reduced-pressure source. The canisters come in varying sizes and designs. The canisters typically need changing or removal on a regular basis. Existing systems for attaching a reduced-pressure source to a canister and for attaching a patient conduit to the canister require considerable attention with the possibility of significant error existing.

SUMMARY

Problems with existing medical canisters and systems are addressed by the illustrative embodiments described herein. According to one illustrative embodiment, a medical canister connector for releasably connecting to a medical canister, which has a patient port and a reduced-pressure port, includes a first connection member for coupling to a first reduced-pressure delivery conduit; a patient-port-attachment member for coupling to the patient port on the medical canister and having a patient-port opening and a first longitudinal axis. The first patient-port-attachment member is coupled to the first connection member. The illustrative medical canister connector further includes a second connection member for coupling to a second reduced-pressure delivery conduit; a reduced-pressure-port attachment member for coupling with a reduced-pressure port on the medical canister and having a reduced-pressure-port opening and a second longitudinal axis; and a spacing member having a first end and a second end. The first end of the spacing member is coupled to the first connection member and the second end of the spacing member is coupled to the second connection member. The medical canister connector has a free position and is operable to be maneuvered into a loading position.

A medical canister connector for releasably connecting to a medical canister, which has a patient port and a reduced-pressure port, includes a first connection member for coupling to a first reduced-pressure delivery conduit and for coupling to a first pressure-sensing conduit; a patient-port-attachment member for coupling to the patient port on the medical canister and having a patient-port opening and a first longitudinal axis. The first patient-port-attachment member is coupled to the first connection member. The medical canister connector further includes a second connection member for coupling to a second reduced-pressure delivery conduit and for coupling to a second pressure-sensing conduit; a reduced-pressure-port-attachment member for coupling with a reduced-pressure port on the medical canister and having a reduced-pressure-port opening and a second longitudinal axis; and a pressure transport member having a first end and a second end. The first end of the pressure transport member is coupled to the first connection member and the second end of the pressure transport member is coupled to the second connection member. The medical canister connector has a free position and the canister is operable to be maneuvered into a loading position.

A method for manufacturing a medical canister connector includes the step of forming a body from a soft thermoplastic polymer to form a medical canister connector. The step of forming a body may include injection molding, thermoforming, thermosettting, overmolding, or substractive machining.

A method for connecting a medical canister, which has a patient port and a reduced-pressure port, to a first reduced-pressure conduit, a first pressure-sensing conduit, a second reduced-pressure conduit, and a second pressure-sensing conduit includes the steps of providing a medical canister connector; providing a flexing force on a pressure transport member of the medical canister connector such that an angle alpha ($\alpha$) formed by intersection of a first longitudinal axis and a second longitudinal axis is greater than 90 degrees and so that a patient-port opening interfaces with a patient port on the medical canister while a reduced-pressure-port opening interfaces with a reduced-pressure port on the medical canister; and releasing the flexing force.

Objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
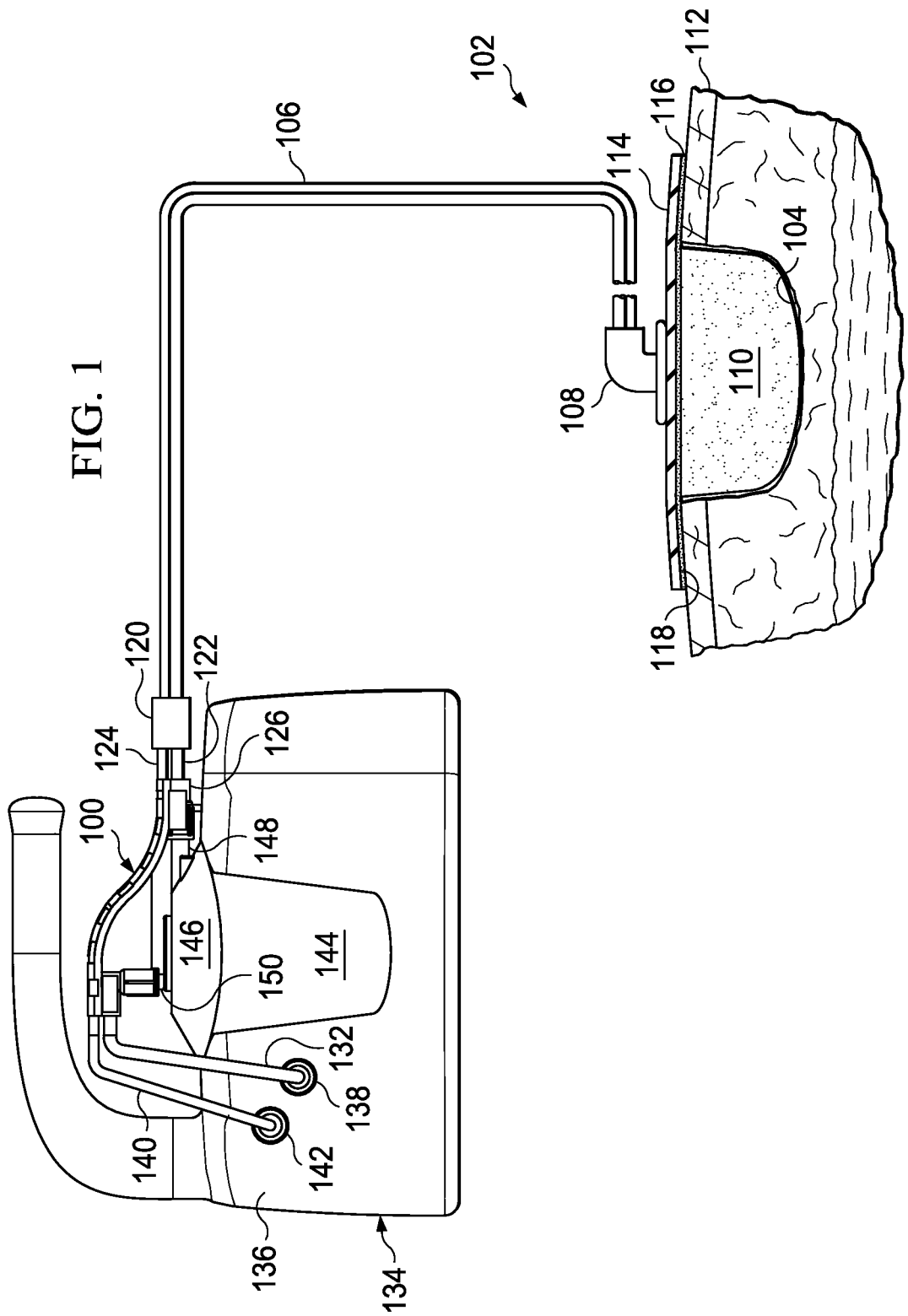
FIG. 1 is schematic diagram, with a portion shown in cross section, of a reduced pressure treatment system and including an illustrative embodiment of a medical canister connector.
Figure 2:
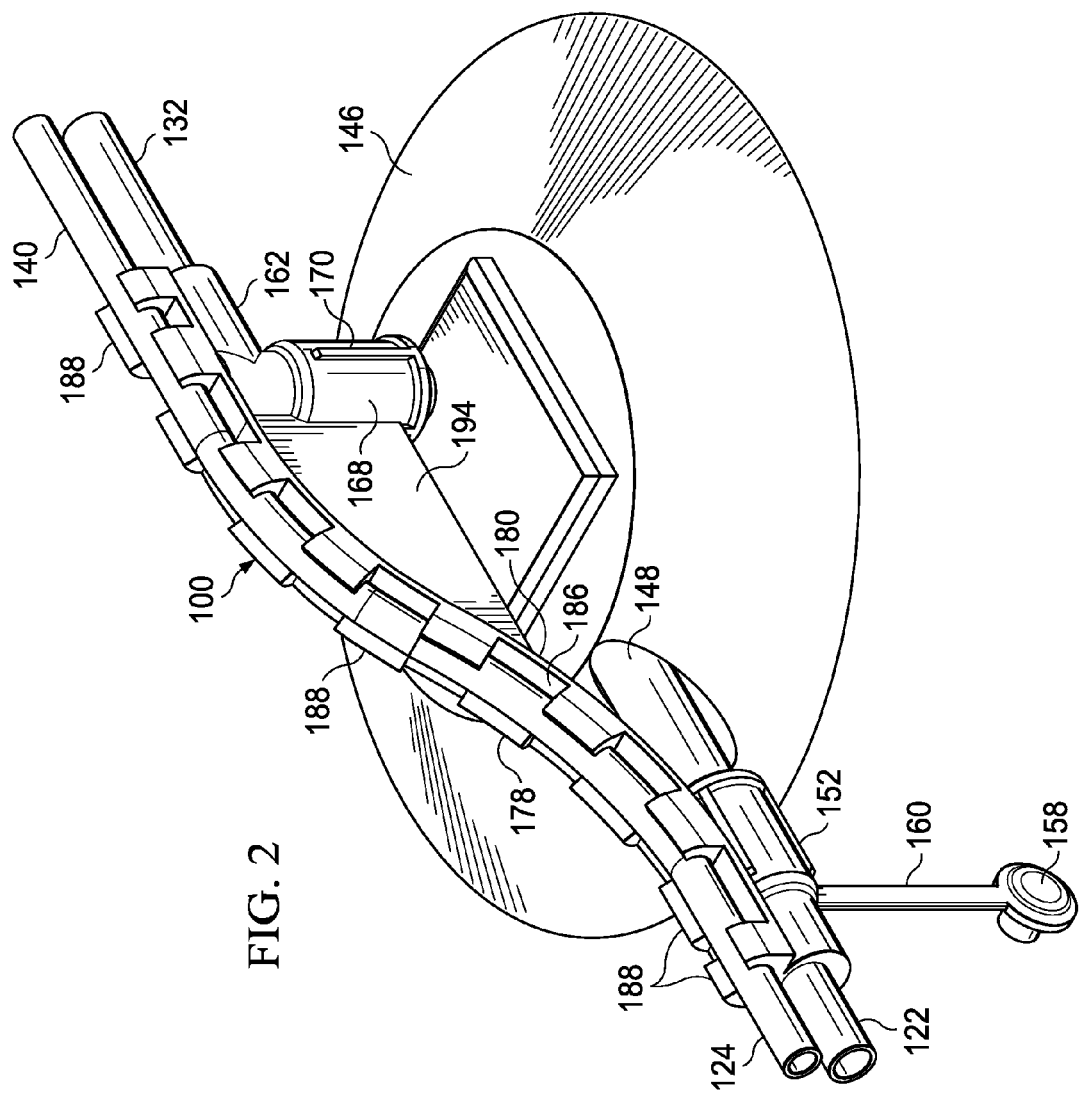
FIG. 2 is a schematic, perspective view of the medical canister connector of FIG. 1 shown on a portion of a medical canister.
Figure 3:
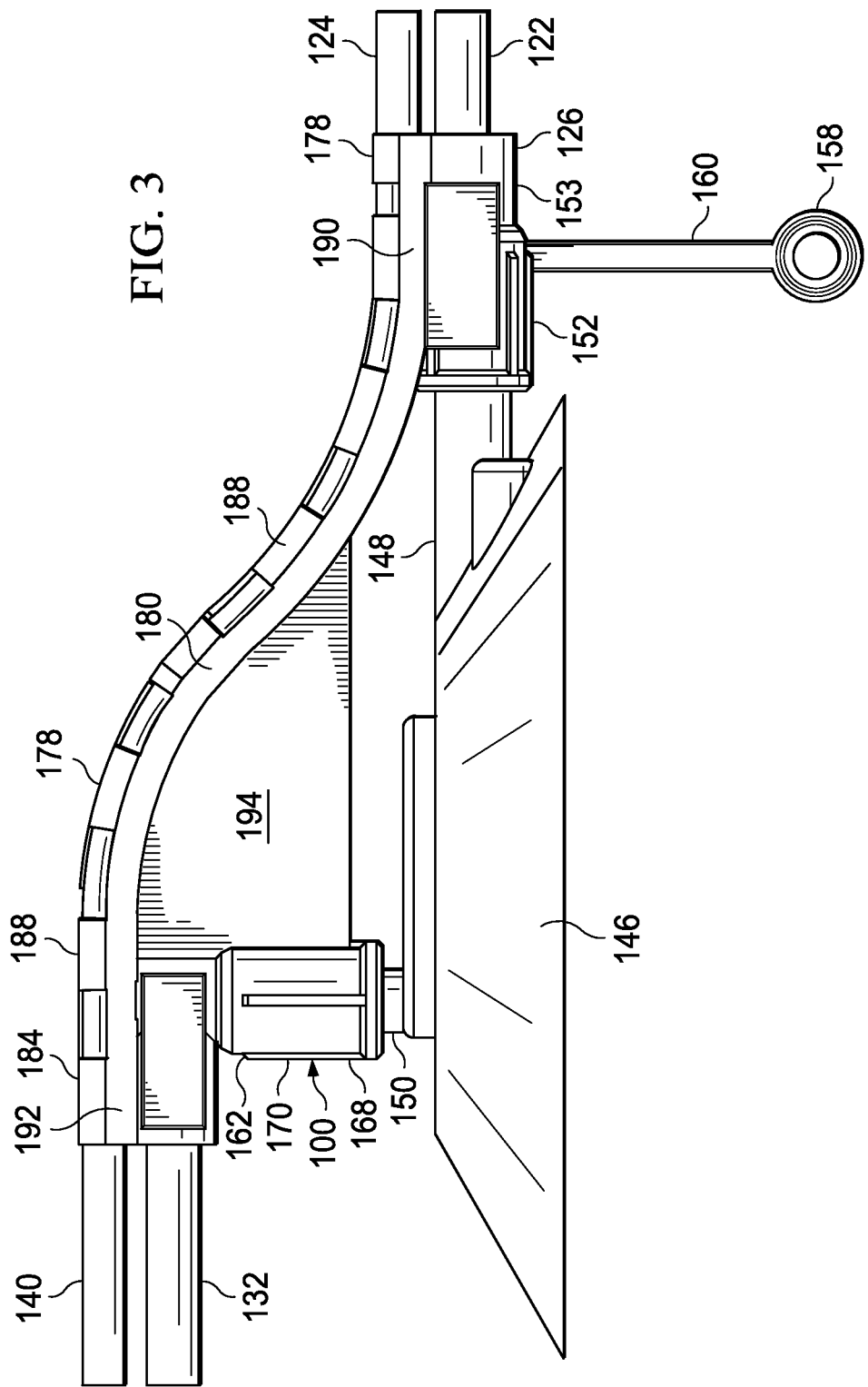
FIG. 3 is a schematic, elevational view of the medical canister connector of FIGS. 1-2.

Referring to FIGS. 1-4, and initially to FIG. 1, an illustrative embodiment of a medical canister connector 100 is shown as part of a reduced-pressure treatment system 102. While the medical canister connector 100 is presented in the context of the reduced-pressure treatment system 102, it should be understood that the medical canister connector 100 might be used with any medical system involving the need to connect conduits to a medical canister. Other examples of medical systems might include a surgical suction system, a medical drainage system, or an open-abdomen reduced-pressure system.

In this illustrative embodiment, the reduced-pressure treatment system 102 provides reduced-pressure treatment to a tissue site 104 on a patient. The tissue site 104 may be the bodily tissue of any human, animal, or other organism, including bone tissue, adipose tissue, muscle tissue, dermal tissue, vascular tissue, epithelial tissue, connective tissue, cartilage, tendons, ligaments, or any other tissue. The tissue site 104 may be within a body cavity, such as an abdominal cavity. The treatment by the reduced-pressure treatment system 102 may include removing fluids, such as ascites or exudates, delivering of reduced pressure, or providing a protective barrier. Unless otherwise indicated, as used herein, "or" does not require mutual exclusivity.

Reduced pressure is delivered through a conduit 106 to a reduced-pressure interface 108. The reduced-pressure interface 108 delivers the reduced pressure to a manifold 110 that is adjacent the tissue site 104. The tissue site 104 is shown as a wound, or damaged area of tissue, that involves epidermis 112 and other tissue layers. A pneumatic seal is formed over the patient's epidermis 112 by a sealing member 114 that has an attachment device 116, such as an adhesive on a patient-facing side 118. The conduit 106 may be a dual-lumen conduit wherein one lumen delivers reduced pressure and transports removed fluids, such as exudates or ascites. The other lumen of conduit 106 may provide a pressure-sensing lumen to allow the pressure at the tissue site 104 to be measured or otherwise determined by a remote measuring device. The conduit 106 could contain additional lumens, but in this example is a dual-lumen design.

The conduit 106 is fluidly coupled to, or in fluid communication with, an interface member 120. The interface member 120 fluidly couples the first lumen to a first reduced-pressure conduit 122 and fluidly couples the second lumen to a first pressure-sensing conduit 124. The first reduced-pressure conduit 122 is coupled to a first connection member 126 of the medical canister connector 100. The first pressure-sensing conduit 124 is also coupled to the first connection member 126.

Figure 4:
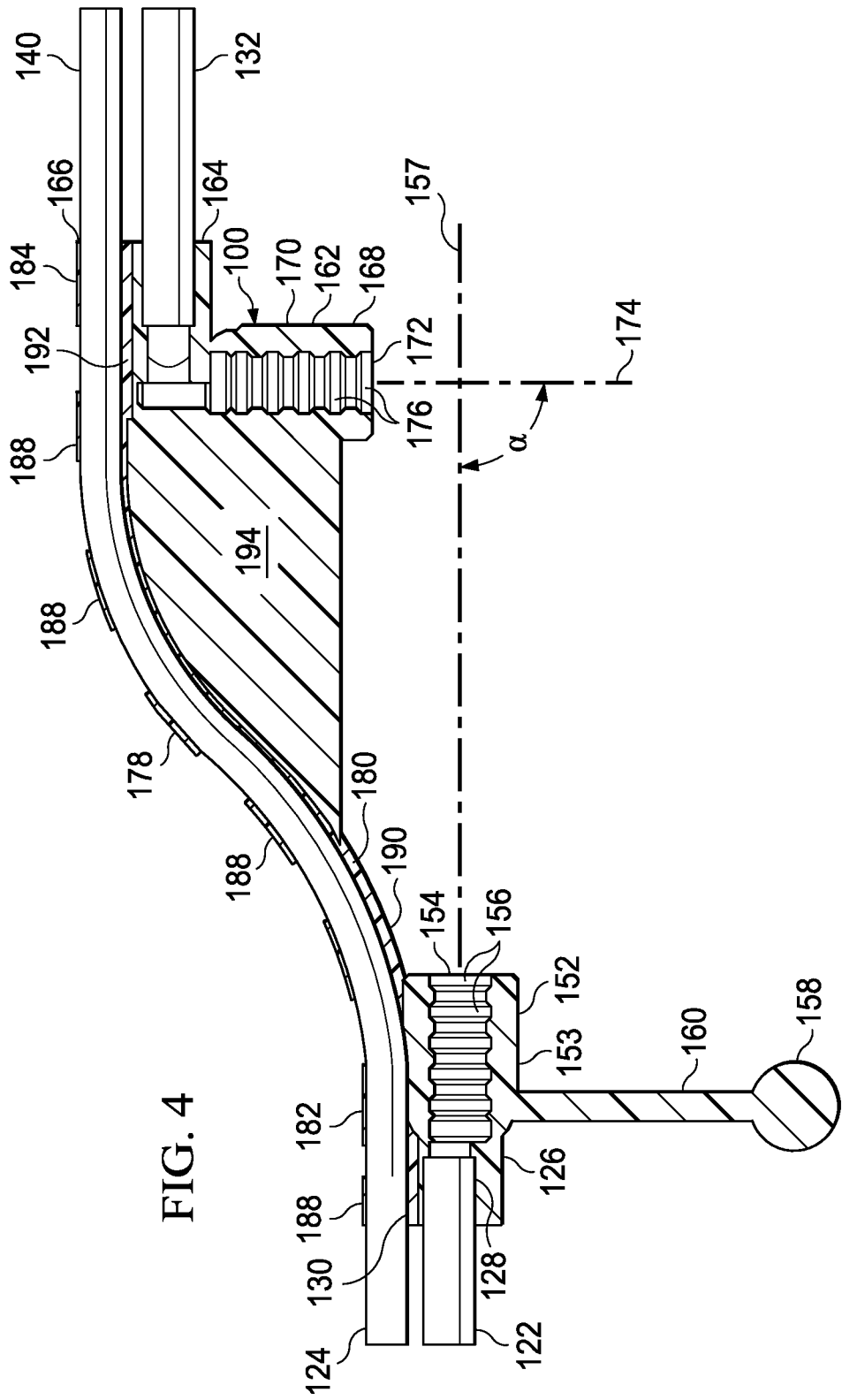
FIG. 4 is a schematic, cross sectional view of the medical canister connector of FIGS. 1-3.

As shown clearly in FIG. 4, the first connection member 126 may be formed with a first reduced-pressure-conduit opening 128 and a first pressure-sensing-conduit opening 130. The first pressure-sensing-conduit opening 130 may be a tubular entry port that receives and surrounds the whole circumference of the first pressure-sensing conduit 124, or the first pressure-sensing-conduit opening 130 may be a channel opening, e.g., could be an extension or part of channel 186, in which only a portion of the circumference of the first pressure-sensing conduit 124 is secured. The first reduced-pressure conduit 122 may be coupled in the first reduced-pressure-conduit opening 128 by solvent bonding, interference fit, adhesive, or other means to achieve a substantially fluid-tight connection. Similarly, the first pressure-sensing conduit 124 may be coupled in the first pressure-sensing-conduit opening 130 by solvent bonding, interference fit, adhesive, or other means.

The medical canister connector 100 is also coupled to a second reduced-pressure conduit 132 that delivers reduced pressure from a reduced-pressure unit 134. The reduced-pressure unit 134 includes a reduced-pressure source, such as a vacuum pump (not shown) or other means of supplying reduced pressure that may be contained within housing 136. The second reduced-pressure conduit 132 enters the housing 136 at a reduced-pressure-housing port 138 and is fluidly coupled to the reduced-pressure source within the reduced-pressure unit 134.

The medical canister connector 100 is also coupled to a second pressure-sensing conduit 140 that delivers pressure to the reduced-pressure unit 134. The second pressure-sensing conduit 140 enters the housing 136 at a pressure-sensing-housing port 142. A measuring device within the housing 136 of the reduced-pressure unit 134 receives the second pressure-sensing conduit 140 and is able to measure or determine the pressure existing at tissue site 104. It should be noted that the first pressure-sensing conduit 124 and the second pressure-sensing conduit 140 may be an integral conduit as is shown.

The medical canister connector 100 facilitates easy connection of the first reduced-pressure conduit 122 and the second reduced-pressure conduit 132 to a medical canister 144 and more particularly to a lid 146 of the medical canister 144. Preferably, a healthcare provider is able to install the medical canister connector 100 to a medical canister 144 with one movement; that is, instead of having to couple two conduits one at a time to two ports, the healthcare provider is able to take hold of the medical canister connector 100 and apply the medical canister connector 100 in one operation to the lid 146. The use of medical canister connector 100 is discussed further below. Moreover, as a safety measure, the medical canister connector 100 is configured so that the first reduced-pressure conduit 122 and second reduced-pressure conduit 132 may only be attached in the proper way without an obvious deviation; this is to minimize or eliminate the possibility of an error being made in treatment. Alternatively, the medical canister connector 100 may transport, e.g., in an internal passageway, the pressure in the first pressure-sensing conduit 124 to the second pressure-sensing conduit 140.

The medical canister 144 may be any canister that requires conduits to be attached accurately and preferably easily. An off-the-shelf medical canister may provide economic advantages for patients and healthcare providers and as such is preferred. The medical canister connector 100 may be sized and configured to work with a particular model of a medical canister. For example, in one illustrative embodiment, the medical canister 144 might be an 800 cc hydrophobic rigid canister, which includes a hydrophobic shutoff filter, available from Beamis Manufacturing Company of Sheboygan Falls, Wis. The medical canister connector 100 will be further explained in the illustrative context of working with this medical canister, but it should be understood that the medical canister connector 100 could easily be used with other off-the-shelf medical canisters by adjusting the dimensions and location of components. The lid 146 of the medical canister 144 has a patient port 148, which is horizontal (for the orientation shown in FIG. 1), and a reduced-pressure port 150, or suction port, which is vertical (for the orientation shown in FIG. 1).

The first connection member 126 is fluidly coupled to the first reduced-pressure conduit 122 and may be fluidly coupled to the first pressure-sensing conduit 124 as previously noted.

A patient-port-attachment member 152 is coupled to the first connection member 126 and formed with a patient-port-attachment body 153 having a patient-port opening 154. The patient-port opening 154 of patient-port-attachment member 152 may be formed with a plurality of sealing ribs 156 to help form an interference fit with the patient port 148 on the medical canister 144. The patient-port opening 154 may also be tapered to further facilitate an interference fit with the patient port 148 on the medical canister 144. In the installed position, the patient-port opening 154 and patient port 148 form a substantially fluid-tight connection. The volume within the patient-port opening 154 has a first longitudinal axis 157.

A stopper 158, or cap, may be coupled with a strap 160 to the first connection member 126, and the stopper 158 may be sized and configured to seal off the patient-port opening 154 when the medical canister connector 100 is not in use or is being changed. Use of the stopper 158 prevents fluids from leaking through patient-port opening 154 when the medical canister connector 100 is not in use or a medical canister 144 is being changed.

A second connection member 162 may be formed with a second reduced-pressure-conduit opening 164 and a second pressure-sensing-conduit opening 166. The second reduced-pressure conduit 132 may be coupled in the second reduced-pressure-conduit opening 164 by solvent bonding, interference fit, adhesive, or other means to achieve a substantially fluid-tight connection. Similarly, the second pressure-sensing conduit 140 may be coupled in the second pressure-sensing-conduit opening 166 by solvent bonding, interference fit, adhesive or other means. The second connection member 162 also includes a reduced-pressure-port attachment member 168 having a reduced-pressure-port body 170 formed with a reduced-pressure-port opening 172. The volume within the reduced-pressure-port opening 172 has a second longitudinal axis 174.

The second reduced-pressure-conduit opening 164 may extend until it intersects the reduced-pressure-port opening 172 and thereby forms a fluid path for reduced pressure to flow into the second reduced-pressure-conduit opening 164 and out of the reduced-pressure-port opening 172. As used herein, "fluid" may include a gas or a liquid. The reduced-pressure-port opening 172 may be formed with a plurality of sealing ribs 176 on an interior surface of the reduced-pressure-port opening 172 to help form an interference fit when the reduced-pressure-port opening 172 is placed on the reduced-pressure port 150 of the lid 146 of the medical canister 144. The interior surface of the reduced-pressure-port opening 172 may also be tapered to further facilitate an interference fit. In the installed position, the reduced-pressure-port opening 172 and the reduced-pressure port 150 achieve a substantially fluid-tight connection.

The first connection member 126 and second connection member 162 may be used to transition conduit sizes. For example, the first reduced-pressure conduit 122 may be a small diameter conduit, but the first connection member 126 allows the first reduced-pressure conduit 122 to be fluidly coupled to a larger diameter patient port 148 on the medical canister 144. The first connection member 126 and second connection member 162 may be used to transition conduit sizes from small to large or large to small.

In one embodiment, the medical canister connector 100 only receives and manages reduced pressure associated with the first reduced-pressure conduit 122 and the second reduced-pressure conduit 132. In this alternative embodiment, the patient-port-attachment member 152 and the reduced-pressure-port attachment member 168 are coupled and secured in a spaced relationship by a spacing member 180.

In another illustrative embodiment, the medical canister connector 100 receives and manages reduced pressure associated with the first reduced-pressure conduit 122 and the second reduced-pressure conduit 132 and the reduced pressure associated with first pressure-sensing conduit 124 and the second pressure-sensing conduit 140. In this illustrative embodiment, the pressure transport member 178 serves as the spacing member and couples and secures in spaced relationship the patient-port-attachment member 152 and the reduced-pressure-port attachment member 168. The pressure transport member 178 facilitates transportation of the reduced pressure between the first pressure-sensing conduit 124 and the second pressure-sensing conduit 140. The transport of the reduced pressure by the pressure transport member 178 may be by an integral chamber or passageway connecting the pressure-sensing conduits 124, 140 or by clips or channels that secure a conduit that fluidly couples the pressure-sensing conduits 124, 140.

The pressure transport member 178 or the spacing member 180 may be used as part of the medical canister connector 100 to hold the first connection member 126 and the second connection member 162 in their relative positions and yet to allow flexibility. The pressure transport member 178 has a first end 182 and a second end 184. The first end 182 of the pressure transport member 178 is coupled to the first connection member 126, and the second end 184 of the pressure transport member 178 is coupled to the second connection member 162. The pressure transport member 178 may be a solid conduit, or passageway, formed in the medical canister connector 100 that transports the pressure from the first pressure-sensing conduit 124 to the second pressure-sensing conduit 140. Alternatively, as shown, the pressure transport member 178 may include a device, e.g., a channel or clip, for holding the first pressure-sensing conduit 124 as the first pressure-sensing conduit 124 runs the length of the medical canister connector 100 to exit at the second pressure-sensing conduit 140. In the latter situation, the pressure transport member 178 may have a channel 186 and a plurality of clips 188 to releasably couple the first pressure-sensing conduit 124/second pressure-sensing conduit 140 to the medical canister connector 100.

Again, in an alternative embodiment, in the situation in which the medical canister connector 100 is for use with only a first reduced-pressure conduit 122 and a second reduced-pressure conduit 132, the spacing member 180 holds the first connection member 126 and the second connection member 162 in their relative positions but does not transport reduced pressure for sensing. The spacing member 180 has a first end 190 and a second end 192. The first end 190 of the spacing member 180 is coupled to the first connection member 126, and the second end 192 of the spacing member 180 is coupled to the second connection member 162. The spacing member 180 may further include a support rib 194 to provide additional strength and stability. When both the pressure transport member 178 and the spacing member 180 are included, the pressure transport member 178 and the spacing member 180 may cooperate to hold the first connection member 126 and the second connection member 162 in their relative positions and to allow flexibility. The pressure transport member 178 and the spacing member 180 may be the same member.

The medical canister connector 100 is formed from a flexible material that allows the medical canister connector 100 to move and twist in a limited manner but adequately to allow the patient-port opening 154 to interface with the patient port 148 on the medical canister 144 while at the same time the reduced-pressure-port opening 172 interfaces with the reduced-pressure port 150 on the medical canister 144. In this way, the medical canister connector 100 is designed to assume at least two positions: a free position in which the patient-port opening 154 and the reduced-pressure-port opening 172 are spaced and aligned to engage the patient port 148 and the reduced-pressure port 150 at the same time, and a loading position in which the medical canister connector 100 is flexed and positioned to allow the patient-port opening 154 to go on to the patient port 148 at the same time that the reduced-pressure-port opening 172 goes on to the reduced-pressure port 150.

One way to describe the flex, or movement, of the medical canister connector 100 in one illustrative embodiment is with reference to the first longitudinal axis 157 and the second longitudinal axis 174. In a two dimensional elevational view, the first longitudinal axis 157 and the second longitudinal axis 174, or at least their projections, intersect to form an angle alpha ($\alpha$). In the free position, the angle alpha ($\alpha$) is about 90 degrees as shown. When flexing the medical canister connector 100 to the loading position, the angle alpha ($\alpha$) may be extended to 95, 100, 110, 120, 130, 140, 150, 160, 170, 180 degrees or more or any angle therein. In addition, the medical canister connector 100 might be twisted axially about the pressure transport member 178 or spacing member 180 or might be twisted about the first longitudinal axis 157 or second longitudinal axis 174. The twisting may be between 1-90 degrees or more.

As previously noted, the medical canister connector 100 is formed from a flexible material that allows the medical canister connector 100 to move and twist. An elastic polymer might be used to form the medical canister connector 100. For example, the medical canister connector 100 may be formed from a soft thermoplastic polymer, such as polyvinyl chloride (PVC), or from a thermoset polymer, such as silicone. Still other polymers and materials, e.g., a flexible composite, might be used as well. The medical canister connector 100 may be formed in a number of ways, such as by injection molding, thermoforming, thermosettting, or overmolding, substractive machining.

There are a number of ways that the medical canister connector 100 may be applied onto the lid 146 of the medical canister 144 and only one illustrative example will now be given. According to one illustrative manner of installing the medical canister connector 100, the healthcare provider may place their hand on the pressure transport member 178 or spacing member 180 to lift the medical canister connector 100 and put the medical canister connector 100 near the lid 146 of canister 144. The patient-port opening 154 may then be maneuvered so that the patient port 148 of the canister lid 146 enters, at least partially, the patient-port opening 154. The healthcare provider may pull, or rotate, on the pressure transport member 178 or spacing member 180. This causes the medical canister connector 100 to flex and causes the angle alpha ($\alpha$) to increase beyond 90 degrees. Then, if not already aligned, the medical canister connector 100 may be twisted about the first longitudinal axis 157 so that the reduced-pressure-port opening 172 aligns with the reduced-pressure port 150 on the lid 146. The healthcare provider may push the patient port 148 a little further into the patient-port opening 154 and release the force on the pressure transport member 178 or spacing member 180 so that the angle alpha ($\alpha$) decreases. As the angle alpha ($\alpha$) decreases, the reduced-pressure port 150 extends further into the reduced-pressure-port opening 172. From there, the healthcare provider may push the medical canister connector 100 further onto the lid 146. The medical canister connector is thus fully connected to the medical canister 144. The medical canister connector 100 attaches to the medical canister 144 in only one way and thereby reduces or eliminates the possibility of error. The medical canister connector 100 may typically be applied by the healthcare provider with one hand.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A method of manufacturing a medical canister connector comprising forming a body from a soft thermoplastic polymer, the body comprising:
    a first connection member for coupling to a first reduced-pressure delivery conduit and for coupling to a first pressure-sensing conduit;
    a patient-port attachment member for coupling to a patient port on the medical canister and having a patient-port opening and a first longitudinal axis, the first patient-port attachment member coupled to the first connection member;
    a second connection member for coupling to a second reduced-pressure delivery conduit and for coupling to a second pressure-sensing conduit;
    a reduced-pressure-port attachment member for coupling to a reduced-pressure port on the medical canister and having a reduced-pressure-port opening and a second longitudinal axis;
    a pressure transport member having a first end and a second end, the first end of the pressure transport member coupled to the first connection member and the second end of the pressure transport member coupled to the second connection member; and
    wherein the medical canister connector has a free position and wherein the canister is operable to be maneuvered into a loading position.

2. The method of manufacturing of claim 1 wherein the step of forming a body from a soft thermoplastic polymer comprises injection molding the body as an integral body.

3. The method of manufacturing of claim 1 wherein the step of forming a body from a soft thermoplastic polymer comprises injection molding the body from polyvinyl chloride (PVC).

4. The method of manufacturing of claim 1 wherein the step of forming a body from a soft thermoplastic polymer comprises injection molding the body from silicone.

5. The method of manufacturing of claim 1 wherein the step of forming a body from a soft thermoplastic polymer comprises thermoforming the body.

6. The method of manufacturing of claim 1 wherein the step of forming a body from a soft thermoplastic polymer comprises thermosettting the body.

* * * * *